United States Patent [19]

Petrofsky

[11] Patent Number: 4,976,264

[45] Date of Patent: Dec. 11, 1990

[54] POWER MUSCLE STIMULATOR

[75] Inventor: Steven H. Petrofsky, Dayton, Ohio

[73] Assignee: Therapeutic Technologies Inc., Tampa, Fla.

[21] Appl. No.: 349,856

[22] Filed: May 10, 1989

[51] Int. Cl.[5] ............................................. A61N 1/00
[52] U.S. Cl. .............................. 128/421; 128/423 W; 128/422
[58] Field of Search ................... 128/421, 422, 423 W, 128/783, 784

[56] References Cited

U.S. PATENT DOCUMENTS

| | | | |
|---|---|---|---|
| 1,908,688 | 5/1933 | Call | 128/421 |
| 2,375,575 | 5/1945 | Morland et al. | 128/421 |
| 2,532,788 | 12/1950 | Sarnoff | 128/421 |
| 3,055,372 | 9/1962 | Browner | 128/421 |
| 3,261,358 | 7/1966 | Bernard | 128/421 |
| 3,954,111 | 5/1976 | Sato | 128/422 |
| 4,177,819 | 12/1979 | Kofsky et al. | 128/421 |
| 4,431,000 | 2/1984 | Butler et al. | 128/421 |
| 4,431,002 | 2/1984 | Maurer et al. | 128/422 |
| 4,535,777 | 8/1985 | Castel | 128/421 |
| 4,724,842 | 2/1988 | Charters | 128/423 W |
| 4,776,852 | 10/1988 | Rubic | 623/26 |
| 4,832,033 | 5/1989 | Maher et al. | 128/421 |

Primary Examiner—Francis Jaworski
Assistant Examiner—George Manuel
Attorney, Agent, or Firm—Wood, Herron & Evans

[57] ABSTRACT

An electrical muscle stimulator is disclosed which provides unloaded isometric exercise of a pair of antagonist muscles associated with a rotatable limb, substantially without creating torque at the rotating joint. Further, a reduced pain stimulus signal is disclosed characterized in that it is continuous, biphasic and camel-back during a fundamental period thereof.

34 Claims, 4 Drawing Sheets

POWER MUSCLE STIMULATOR

BACKGROUND OF THE INVENTION

I. Field of the Invention

The present invention relates to functional electrical stimulation (FES) of muscles to induce contraction thereof with electrical stimulus. More specifically, the present invention relates to electrically stimulating and exercising muscles to build muscle mass and, more particularly, isometric exercise of muscles associated with a limb which is adapted to rotate at a joint.

II. Background of the Invention

Much work has been done in the area of functional electrical stimulation of muscles. Most notably, substantial success has been achieved in the area of building muscle mass of nerve-disabled individuals such as paraplegics and/or quadriplegics by electrically stimulating the muscles sufficient to induce work-producing contraction of the muscles ("power contraction").

By way of example, U.S. Pat. No. 4,499,900, the disclosure of which is hereby incorporated herein by reference, discloses an exercise bicycle which utilizes functional electrical stimulation to induce sufficient contraction of lower trunk and leg muscles of a nerve-damaged individual such that the legs of that individual pedal an exercise bicycle thereby exercising otherwise atrophy-prone muscles. Because limbs are in motion, the exercise is referred to as isotonic.

Similar systems have been developed to provide isometric exercise of muscles, i.e., the associated limbs are not generally in motion. Characteristic of isometric exercise is that the limb is externally restrained from, or loaded against, rotation which would otherwise occur thus creating substantial torque at the joint about which the limb normally rotates. Prior art isometric exercise systems which utilized FES similarly restrained or loaded the involved limb. For example, U.S. Pat. Nos. 4,480,830 and 4,492,233, the disclosures of which are hereby incorporated herein by reference, disclose providing functional electrical stimulation to the muscles of a patient's leg to induce rotation of the lower leg at the knee joint. The ankle is restrained in one example so that the lower leg will not rotate. However, substantial torque may be created at the knee joint. To avoid over-torqueing the knee or damaging the limb of the lower leg and/or the knee joint, therefore, the level of electrical stimulation used for the isometric exercise must necessarily be limited. Consequently, loaded isometric exercise may impose limits on how much beneficial exercise can be obtained to build up muscle mass.

In systems of the prior art adapted to provide power contraction of human muscle, the electrical stimulus coupled to the muscle typically has characteristics which, if applied to an individual without severe nerve damage associated with the muscles to be stimulated, could cause excruciating pain. Thus, individuals who are either not nerve-damaged or have only partial (but relevant) nerve-damage may not be able to take full advantage of functional electrical stimulation without risking severe pain. Thus, use of prior art "power contracting" type of systems have generally been limited to paraplegics and/or quadriplegics. However, many individuals, not just those suffering from severe nerve damage, could benefit from electrically-induced power contraction exercise therapy.

SUMMARY OF THE INVENTION

The present invention provides a power muscle stimulator which overcomes drawbacks associated with prior art isometric power contraction systems. In accordance with principles of the present invention, isometric exercise of muscles associated with a rotatable limb is accomplished in a manner creating little or no torque at the joint at which that limb rotates and without the need to externally restrain or load the limb. To this end, and in its broadest sense, the present invention provides simultaneous power contraction of an agonist muscle and a related antagonist muscle associated with a limb to thereby achieve unloaded isometric exercise. Power contraction of the agonist muscle tends to rotate the limb in a first direction while power contraction of the antagonist muscle tends to rotate the limb in a second but opposite direction. The level of contraction of the respective muscles is effective to cause substantially equivalent contraction of the agonist and antagonist muscles, i.e., tendency of the limb to rotate in one direction is offset by a substantially equal tendency to rotate in the other direction. Consequently, the limb is internally restrained from rotation by the substantially equivalent, but oppositely acting, power contractions of the muscle pair such that the muscles are stimulated substantially without creating torque at the joint. The relatively torque-free joint thus allows substantially greater electrical stimuli level for isometric exercising than is believed to have previously been applied.

More specifically, the present invention contemplates substantially simultaneously (1) applying a first electrical stimulus to an agonist muscle associated with the limb to contract the agonist muscle whereby to tend to rotate the limb in one direction relative the joint of the limb about which the limb is rotatable, and (2) applying a second electrical stimulus to an antagonist muscle associated with the limb to contract the antagonist muscle whereby to tend to rotate the limb in another, opposite direction relative the joint wherein the first and second electrical stimuli have respective characteristics effective to cause contraction of the respective muscles in an amount such that tendency of the limb to rotate in one direction is offset by a substantially equal tendency to rotate in the opposite direction whereby to isometrically stimulate the muscles substantially without creation of torque at the joint. The two electrical stimuli preferably have identical waveshape characteristics.

In accordance with an aspect of the invention, the first and second electrical stimuli may be generated from the same or common stimulus generator so that they occur simultaneously and with similar characteristics. To adjust contraction levels of the respective muscles, the output of the stimulus generator may be amplified through a pair of parallel, but independently amplitude-adjustable, channels to thereby generate the first and second electrical stimuli for application to the muscle pair. In accordance with a further aspect of the invention, the common stimulus generator may include a waveform generator adapted to generate one of a number of selected, relatively high frequency waveform signals which is then multiplied by a relatively low frequency profile signal from a profile generator adapted to generate one of a number of selected profile signals. The output of the multiplied signal may then be coupled through the above-mentioned channels to the muscle pair whereat the muscles are stimulated by the high frequency waveform signal and at various levels in accordance with the profile signal.

The high frequency waveform signal preferably includes a stim segment and a rest segment, the stim segment being the basis for actual stimulation of muscles. The stim segment is, therefore, preferably selected to maximize training or the effective building of muscle mass. The stim segment is further preferably selected to minimize the risk of pain associated with use of the power muscle stimulator of the present invention. Such a selection is especially advantageous where the invention is to be employed on humans who might otherwise suffer severe pain with electrically-induced power contraction of the muscles, such as those who have little or no nerve damage associated with the muscles to be exercised.

It is known that pain is reduced by the use of a continuously varying biphasic (having generally positive and negative amplitude portions relative an average or reference separated by one zero-crossing of the reference during any one fundamental period) electrical stimuli such as is produced by a sinewave. Thus, one possible waveform signal which may be employed in the present invention has a stim segment which, over a fundamental period, is a simple sinewave.

In accordance with a yet further aspect of the present invention, a preferred stim segment is provided for use of the invention even for individuals suffering from little or no nerve damage. While sinewave stim segments may allow non-nerve injured individuals to obtain some of the benefits of the present invention, the sinewave stim segment may still create an objectionable level of pain at maximum electrical stimulus levels. The preferred stim segment is, thus, provided to allow for power contracting electrical muscle stimulation with reduced risk of pain, even for individuals suffering no relevant nerve damage.

The preferred stim segment has a fundamental period during which a continuous, camel-back, biphasic signal is generated. More specifically, the preferred stim segment is continuous and biphasic, but has three portions separated by two zero crossings, relative an average or reference, rather than two portions separated by one zero crossing as would occur with a sinewave stim segment. Further, the first and third portions of the continuous, camel-back, biphasic stim segment are substantially identical in duration and magnitude relative the reference, while the second, intermediate portion is selected to have a duration equal to the sum of the duration of the first and third periods but a magnitude equal and of opposite polarity to the magnitude of either the first or third portions. As a consequence, the total energy output of both the first and third portions is equal, but of opposite polarity to the total energy output of the second portion. The preferred stim segment of the present invention is believed to be sufficient to power contract human muscle with little discomfort and with substantially reduced pain as compared to the sinewave stim segment, for example, such that muscles of non-nerve damaged individuals may be exercised with functional electrical stimulation with reduced risk of pain or worse.

These and other objects and advantages of the present invention shall become more apparent from a detailed description of the invention.

BRIEF DESCRIPTION OF THE DRAWINGS

The accompanying drawings, which are incorporated in and constitute a part of this specification, illustrate the invention and, together with the general description of the invention given above and the detailed description given below, serve to explain the principles of the invention.

DETAILED DESCRIPTION OF THE INVENTION

Figure 1:
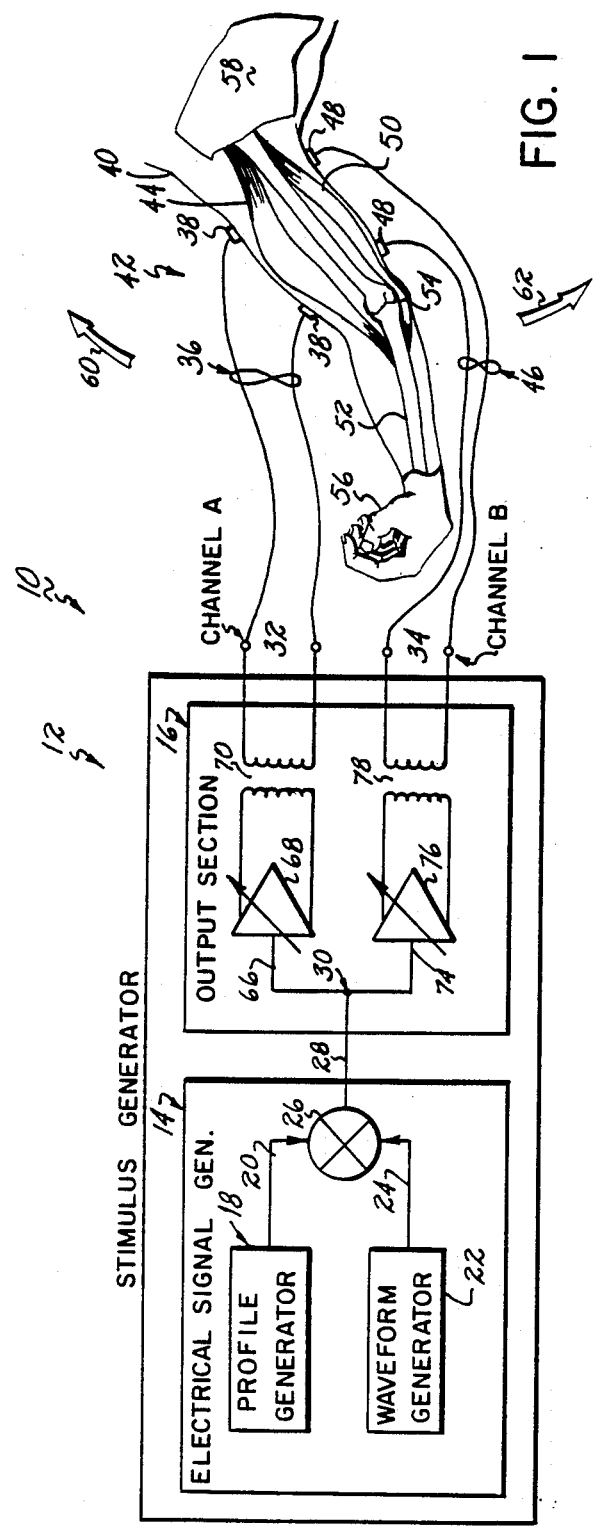
FIG. 1 is a block schematic diagram of an isometric power muscle stimulator used in accordance with principles of the present invention.

With reference to FIG. 1 there is shown a power muscle stimulator 10 adapted to provide isometric muscle exercising in accordance with the principles of the present invention. Power muscle stimulator 10 includes a stimulus generator 12 having an electrical signal generator 14 and an output section 16. Electrical signal generator 14 includes a digital synthesis profile generator 18 to produce a profile signal on output 20, and a digital synthesis waveform generator 22 to produce a waveform signal on output 24. Profile signal 20 and waveform signal 24 are combined as at multiplier 26 to provide on output 28 of electrical signal generator 14 a combined generator output signal which is coupled to output section 16.

Output section 16 splits generator signal 28 at node 30 to follow two parallel paths whereby to simultaneously generate power-contracting electrical stimulus signals at channel A output 32 and channel B output 34, respectively. Stimulus signals 32 may be coupled over a pair of wires 36 to a pair of surface electrodes 38 placed on the skin 40 of a human's arm 42 in overlying relationship with the biceps muscles 44 thereof. Similarly, stimulus signal 34 may be coupled over a second pair of wires 46 to a second pair of surface electrodes 48 placed on the skin 40 in overlying relationship with the triceps muscles 50 of arm 42. The forearm limb 52 (e.g., the ulna and radius) is adapted to rotate about the elbow 54 in at least a folding direction (hand 56 moves toward clavicle 58) and an opposite folding direction (hand 56 moves away from clavicle 58), as indicated by arrows 60, 62, respectively. As will be appreciated, biceps and triceps muscles 44, 50 form a pair of antagonist muscles (one muscle being the agonist and the other muscle being the antagonist), that is, respective contraction of biceps and triceps muscles 44, 50 will tend to rotate limb 52 in opposite directions. Thus, application of stimulus signal 32 to biceps muscles 44 will contract same whereby to tend to rotate limb 52 in the direction of arrow 60. Similarly, application of stimulus signal 34 to triceps muscles 50 will contract same whereby to tend to rotate limb 52 in the direction of arrow 62.

As the stimulus signals 32, 34 are generated substantially simultaneously, muscles 44, 50 will contract substantially simultaneously as well, such that tendency of forearm 52 to rotate in one direction is offset by a tendency of forearm 52 to rotate in the opposite direction. To allow for isometric exercise of muscles 44, 50, substantially without creation of torque at elbow 54, tendency of forearm 52 to rotate in the two opposite directions should be maintained in general equipoise. This may be accomplished by independently adjusting the amplitude of stimulus signals 32, 34 so that the amount of contraction of the respective muscles may be appropriately selected for isometric exercise of the muscles of the forearm with a substantially torque-free elbow joint.

To this end, generator signal 28 is coupled to the input 66 of gain adjustable amplifier 68 which, in conjunction with transformer isolator 70, produces the electrical stimulus signal at channel A output 32, having a constant current preferably adjustable between 0 and 80 milliamps. Similarly, generator signal 28 is also coupled to the input 74 of a second, gain adjustable amplifier 76 which, in conjunction with transformer isolator 78, provides the electrical stimulus signal at channel B output 34, also having a constant current preferably adjustable between 0 and 80 milliamps. Adjustment of the current output level of stimulus signals 32, 34 is accomplished by varying the gain of respective amplifiers 68, 76. The amount of contraction of muscle pairs 44, 50 may, thus, be appropriately selected to cause forearm 52 to remain substantially stationary, notwithstanding tendency of forearm 52 to rotate in either direction 60 or direction 62 due to stimulation of muscle pairs 44, 50. Hence, muscle pairs 44, 50 may be power contracted and exercised without creation of much, if any, torque at elbow 54. As a consequence, significant power contraction of biceps muscle 44 and triceps muscle 50 may be achieved to advantageously build up substantial muscle mass without loading the forearm. Further, such contraction may be achieved at higher stimulation levels than is believed to have been previously applied in loaded isometric exercises employing functional electrical stimulation and without risking grave injury to forearm 52 and/or elbow 54.

Figure 2:
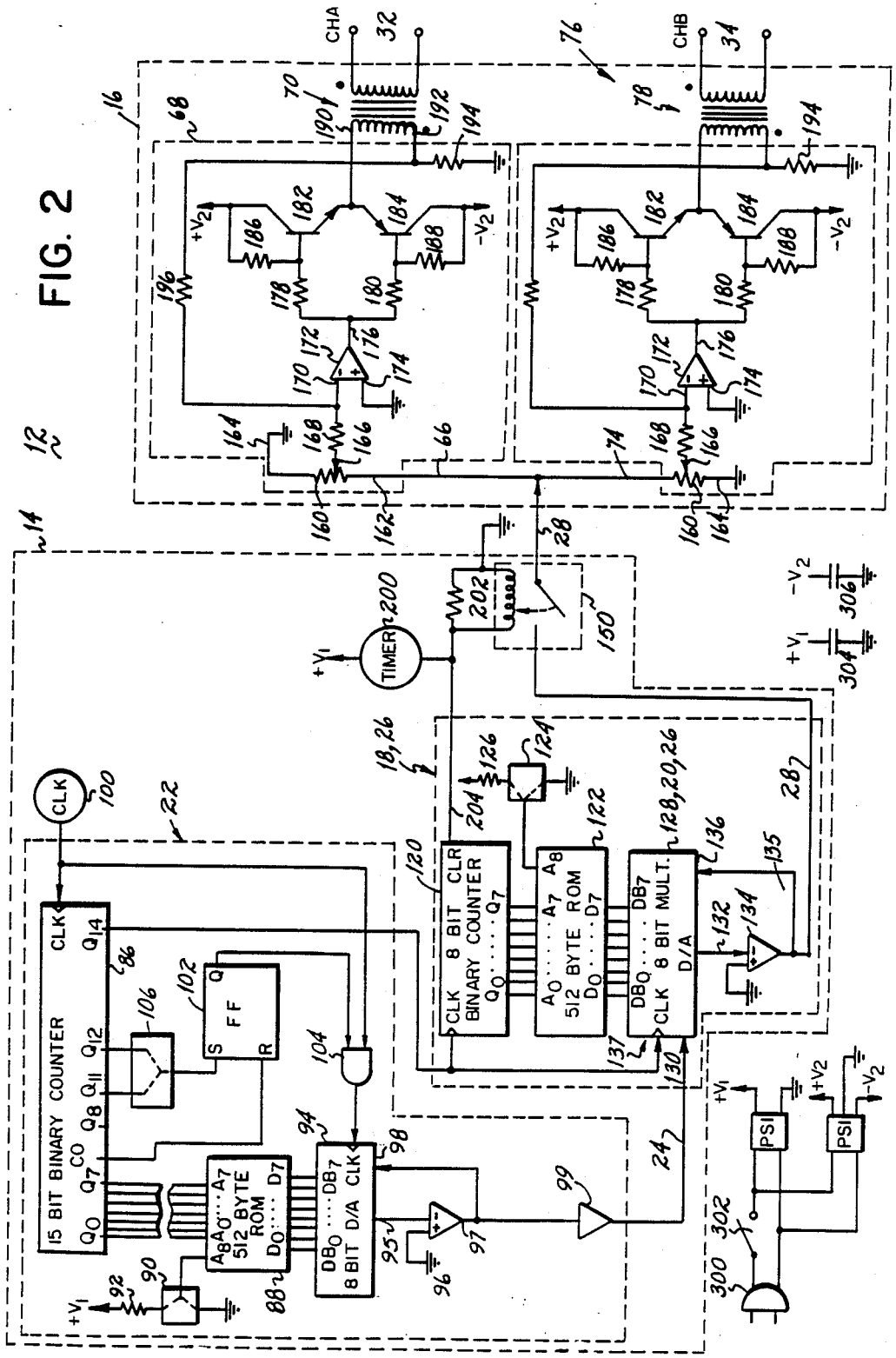
FIG. 2 is a more detailed schematic diagram of an embodiment of the stimulator of FIG. 1.

With further reference to FIG. 2, there is shown a more detailed schematic of an embodiment of the power muscle stimulator 10. Waveform generator 22 includes a 15-bit synchronous binary counter 86 (such as four cascaded 4-bit synchronous binary counters with the clear inputs tied to $+V_1$ to provide a 16-bit counter with only the first fifteen-bits utilized). The first eight outputs ($Q_0$–$Q_7$) of counter 86 are utilized to select the lower order address lines ($A_0$–$A_7$) of a 512-byte (or word) memory 88 such as a read-only-memory (ROM) or a programmable-read-only memory (PROM). The higher order address line ($A_8$) of memory 88 may be selected via a stim segment selector switch 90. In one position of switch 90, the higher order address line is coupled to ground whereby outputs $Q_0$–$Q_7$ of counter 86 address a first portion or page of memory 88 wherein a first stim segment is digitally represented. Switch 90 has a second position wherein the higher order address line of memory 88 is coupled to $+V$ through a resistor 92, whereby outputs $Q_0$–$Q_7$ of counter 86 address a second portion or page of memory 88 wherein a second stim segment is digitally represented. The eight data outputs of memory 88 ($D_0$–$D_7$) are coupled to the data inputs ($DB_0$–$DB_7$) of a clocked 8-bit digital-to-analog (D/A) converter 94 such as a Part NO. AD7524 available from Analog Devices, Norwood, Mass. If such a multiplying D/A converter is used, the $V_{REF}$ input is preferably coupled directly to $+V_1$. The analog output 95 of converter 94 is amplified by operational amplifier 96 in conjunction with feedback of the output 97 from amplifier 96 to the $R_{feedback}$ pin 98 of converter 94. The output 97 is coupled to a level shifting operational amplifier 99 to generate a biphasic waveform signal 24 having both positive and negative amplitude portions relative ground. Amplifier 99 is preferably configured to provide a low pass filter function such as with RC feedback (not shown) to have a cutoff of approximately 14 KHz to reduce noise from waveform generator 22.

Clock 100 generates pulses (e.g., at 250 KHz) to counter 86 causing it to increase its count such that outputs $Q_0$–$Q_7$ repeatedly cycle between a binary count of 0 and 256, whereby to consecutively address memory word locations 0 to 256 on a selected page of memory 88. Stored within memory word locations 0 to 256 on a page of memory 88 are digital representations of the stim segment of the waveform signals desired to be applied to muscles 44, 50 to affect isometric exercise thereof. The clock rate is selected so that the entire selected page of memory 88 is read out over a period of about 1,000 microseconds and, more specifically, 976.5 microseconds. Thereafter, there is a rest segment after which the stim segment is again generated from memory 88. The rest period is controlled by flip-flop 102, NAND gate 104 and rep rate switch 106, as will be described shortly. Depending upon the data programmed into the selected page of memory 88, there may also be periods of rest during the stim segment whereby the fundamental period of active (non-zero) portion of the stim segment may be varied.

Flip-flop 102 is set by a higher order output pulse from counter 86 causing flip-flop 102's output (Q) to go high, thereby enabling NAND gate 104. While NAND gate 104 is enabled, clock pulses from clock 100 are coupled to write input of D/A converter 94 (the chip select input is preferably tied to ground), whereby to latch the converter 94 in synchronization with each change in data from memory 88 which, in turn, changes with each clock pulse as the count of counter 86 is incremented. At the end of the count to 256, a carry-out between outputs $Q_7$ and $Q_8$ of counter 86 (such as a carry-out "CO" from the second of the four cascaded counters) is coupled to flip-flop 102, thereby resetting same and driving its output Q low. In turn, NAND gate 104 is disabled driving the output of D/A converter to zero for a rest segment.

Flip-flop 102 remains reset (output Q is low) until the flip-flop receives a set signal from a higher order output of counter 86. Preferably, $Q_{11}$ or $Q_{12}$ provide the set signal to flip-flop 102 to define a 30 Hz or 60 Hz rep rate to the waveform signal. The rep rate is determined by the position of a rep rate switch 106 which selectively couples output $Q_{11}$ or $Q_{12}$ of counter 86 to the set input of flip-flop 102. Consequently, NAND gate 104 will be enabled every 1/30 of a second (if output $Q_{11}$ of counter 86 is selected) or every 1/60 of a second (if output $Q_{12}$ of counter 86 is selected), whereupon the output of D/A converter 92 will again provide an analog output corresponding to the selected stim segment data from memory 88 at a repetition rate determined by the position of switch 106. Although not shown, circuitry may be provided between switch 106 and flip-flop 102 correlating the set signal to the clock signal to ensure that the stim segment is begun at the correct time relative the clock and the counter.

Figure 3:
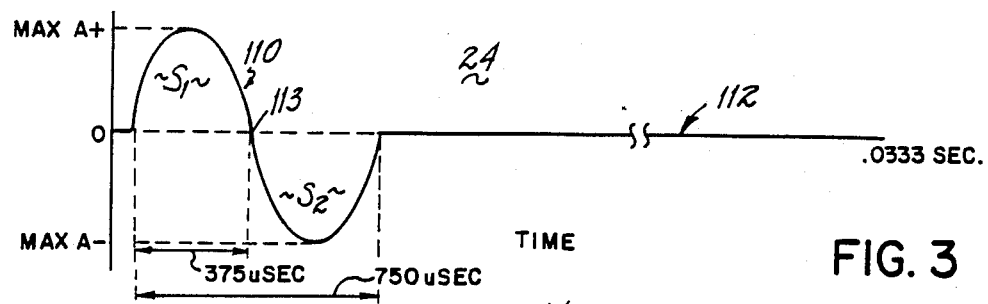
FIG. 3 is an exemplary waveform signal generated by the waveform generator of FIG. 1.
Figure 6:
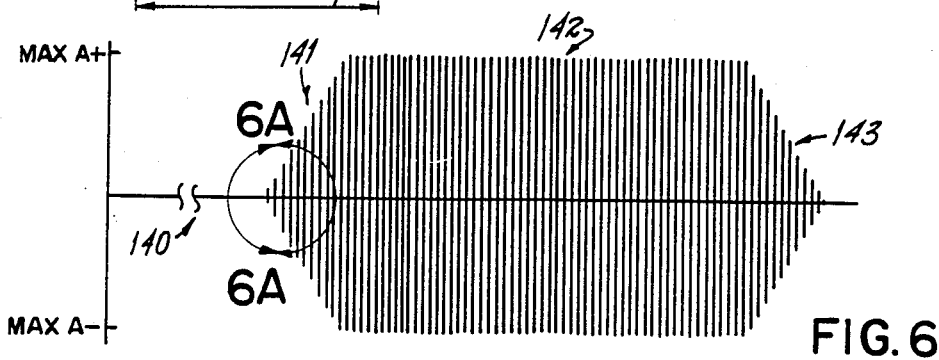
FIG. 6 shows a representative, exemplary generator output signal and/or stimulus signal obtained when the waveform signal of FIG. 3 is multiplied by the profile signal of FIG. 4.

An exemplary waveform signal 24 produced by waveform generator 22 with a selected non-zero amplitude stim segment 110 and a zero-amplitude rest segment 112 is shown in FIG. 3. Stim segment 110 is a continuous sinewave during one fundamental period thereof and has two portions $S_1$ and $S_2$ of opposite polarity relative the reference of zero (separated by a zero crossing 113) thereat. The amplitude of portions $S_1$ and $S_2$ are of equal magnitude, but opposite sign. Although portion $S_1$ is shown as positive relative the zero reference and $S_2$ is negative, an inverse sinewave could be utilized for stim segment 110 (portion $S_1$ negative and portion $S_2$ positive). In any event, stim segment 110 is shown as having approximately a 1.3 KHz fundamental frequency. The duration of the rest segment 112 (and any leading and/or trailing rest portion of the stim segment 110) is selected so that together with the duration of stim segment 110, waveform signal 24 has a repetition rate defined as either about 30 Hz or about 60 Hz. Other frequencies and/or rates could be selected, but these are preferred. The FIG. 3 exemplary waveform signal is shown as having an approximately 30 Hz repetition rate such that segments 110 and 112 are shown as totaling about 1/30 second. An alternative stim segment 114 is shown in FIG. 6 to be discussed, along with FIG. 3, in more detail hereinafter.

Profile generator 18 is similar to waveform generator 22 in that it includes an 8-bit counter 120 (such as two cascaded 4-bit counters), the outputs ($Q_0$–$Q_7$) of which address the lower order address lines ($A_0$–$A_7$) of a 512-byte (or word) memory 122 such as a ROM or a PROM. Similarly, the higher order address line ($A_8$) of memory 122 may be selected via a profile selector switch 124. In one position of switch 124, the higher order address line is coupled to ground whereby the outputs of counter 120 address a first portion or page of memory 122 wherein a first profile signal is digitally stored. In a second position of switch 124, the higher order address line of memory 122 is coupled to $+V_1$ through a resistor 126 whereby the outputs of counter 120 address a second portion or page of memory 122 wherein a second profile signal is digitally stored.

The eight data outputs of memory 122 ($D_0$–$D_7$) are coupled to the data inputs ($DB_0$–$DB_7$) of a clocked 8-bit multiplying D/A converter 128 (again, such as Part No. AD7524, available from Analog Devices with the $\overline{\text{chip select}}$ pin tied low) to produce within D/A converter 128 the profile signal 20 in accordance with data from memory 122. Additionally, waveform signal 24 from waveform generator 22 is coupled to the $V_{REF}$ input 130 of D/A converter 120. D/A converter thus acts as multiplier 26 to multiply waveform signal 24 by the internally generated profile signal 20 to provide an analog signal at output 132. Output 132 is coupled to operational amplifier 134 which, in conjunction with feedback of its output 135 to the $R_{feedback}$ input 136 of D/A converter 128 produces generator signal 28.

Counter 120 of profile generator 18 and $\overline{\text{write}}$ pin 137 of converter 128 are responsive to the $Q_{14}$ output of counter 86 of waveform generator 22 whereby counter 120 is clocked at a rate such that it counts from 0 to 256 once every approximately 30 seconds and then repeats to address the corresponding address locations in the selected page of memory 122 as converter 128 produces the analog output. Accordingly, profile signal 20 has an extremely low repetition rate relative the repetition rate of the waveform signal and the even higher frequency of the stim segment thereof. The profile signal may thus be utilized to provide an overall amplitude profile to the electrical stimulus to be applied to the muscles.

Figure 4:
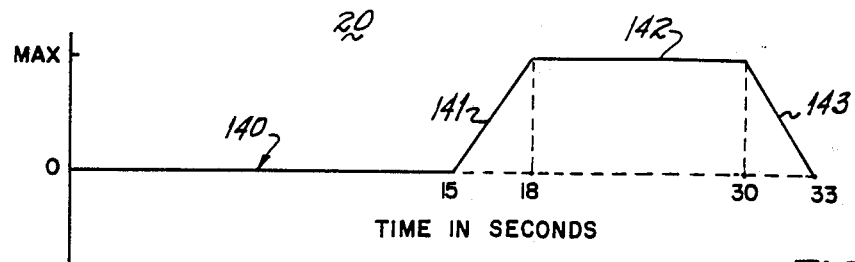
FIGS. 4 and 5 are exemplary profile signals generated by the profile generator of FIG. 1.

A digital representation of a first exercise profile signal may be stored in locations 0 to 256 of one page of memory 112 as shown in Table I. The first exercise profile signal is designed to develop slow twitch muscles which provide endurance. To this end, the first or slow twitch profile signal preferably consists of (1) a period of zero amplitude (i.e., the muscles rest); followed by (2) an increasing amplitude ramp during which the amount of each muscle contraction is to increase to warm up the muscles and/or reduce pain, (3) a period of full amplitude for maximum exercise of the muscles, and (4) a decreasing amplitude ramp during which the amount of each muscle contraction is to decrease to relax the muscles. With reference to FIG. 4, an exemplary slow twitch exercise profile signal is shown which preferably starts off with 15 seconds of zero or rest (140), then increases or ramps up uniformly for 3 seconds to a maximum (141). The maximum level (142) is maintained for 12 seconds and then the level ramps down (143) over a period of 3 seconds to zero.

Figure 5:
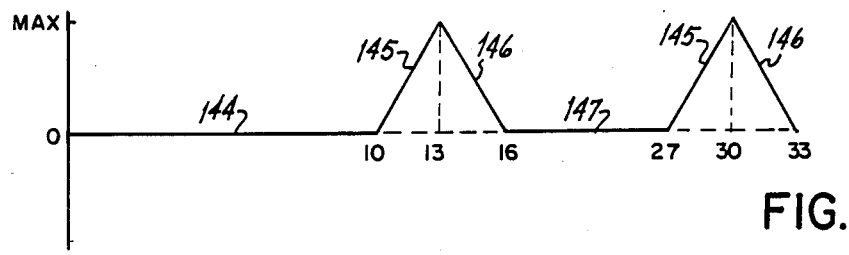

A second profile signal may be digitally represented in a second page of memory 112 as shown in Table II. The second profile signal is designed to develop fast twitch muscle fibers which provide strength. This second or fast twitch profile signal preferably consists of at least one zero-amplitude rest period followed by (1) an increasing amplitude ramp and immediately followed by decreasing amplitude ramp. With reference to FIG. 5, an exemplary fast twitch exercise profile signal is shown which preferably starts off with 10 seconds of zero or rest (144), then increases or ramps up uniformly for 3 seconds to a maximum (145), then ramps down uniformly for 3 seconds to zero (146), followed by a second rest period of 11 seconds (147), which is then followed by a repeat of three second ramp-up 145 and three second ramp-down 146.

The resulting output, i.e., generator signal 28, produced by the combined effects of profile and waveform generators 18, 22 is coupled to the output section 16 for amplification and application to the muscles as stimulus signals 32, 34. These stimulus signals have a waveshape generally identical to the waveshape of generator signal 28, but with possibly different amplitudes in terms of voltage and/or current.

Figure 6A:
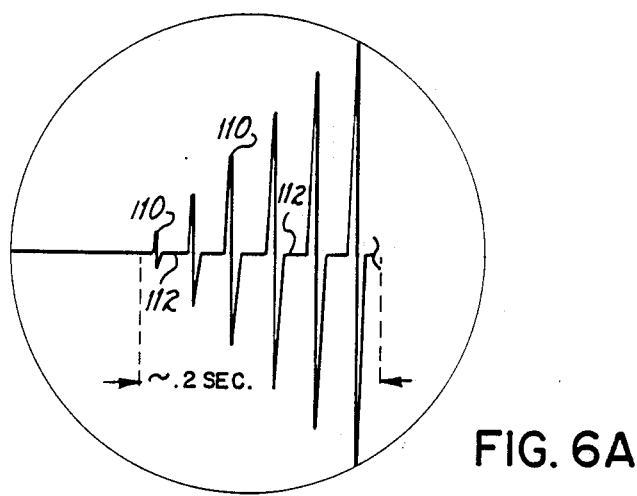
FIG. 6A is an expanded view of the portion of FIG. 6 encircled by lines 6A—6A.

An exemplary generator signal 28 is shown in representative form in FIG. 5. As a result of combining the waveform signal of FIG. 3 and the profile signal of FIG. 4, the generator signal (and, thus, the corresponding stimulus signals) has a relatively long rest period 140, a period 141 of increasing amplitude high frequency stim segments 110 separated by brief inter-stim segment rest segments (112) (see FIG. 6A), a relatively long period 142 of maximum amplitude high frequency stim segments 110 and related, brief rest segments 112, and then concluding with a period 143 of diminishing amplitude stim segments 110 and related brief rest segments 112. The first approximately two-tenth second of the ramp-up period 141 is shown in FIG. 6A for clarification.

To couple generator signal 28 to the muscle as stimulus signals 32, 34, the generator signal is coupled via relay switch 150 to substantially identical amplifiers 68 and 76 of output section to isometrically exercise muscles 44, 50 having a waveform corresponding to generator signal 28 and amplitudes selected by the gain of amplifiers 68 and 78.

Each of amplifiers 68, 76 includes a 10 kilohm input potentiometer 160, one terminal 162 of which is coupled to signal 28 at node 30 and the other terminal 164 of which is coupled to ground. The wiper 166 of potentiometer 160 is coupled through a 4.75 kilohm resistor 168 to the inverting input 170 of an operational amplifier 172. The non-inverting input 174 of amplifier 172 is coupled to ground. Output 176 of amplifier 172 is coupled through parallel 2 kilohm resistors 178, 180 to the base of NPN transistor 182 and PNP transistor 184, respectively. The collector of transistor 182 is coupled to $+V_2$, while the collector of transistor 184 is coupled to $-V_2$. The base of transistors 178, 180 are further coupled to $+V_2$ and $-V_2$, respectively, through 20 kilohm resistors 186, 188, respectively. The emitters of transistors 182, 184 are coupled together and to an input terminal 190 of a respective isolation transformer 70 or 78. The other terminal 192 of the transformer 70 or 78 is coupled to ground through a 1 ohm resistor 194 and to input 170 of amplifier 172 through 1.15 kilohm resistor 196 to thereby provide variable gain feedback to amplifier 172.

Depending upon the setting of input potentiometer 160, the emitters of transistors 182, 184 will output a constant current between 0 and 80 milliamps commanded to an external load of 50 ohms to 1500 ohms. Transformers 70, 78 are preferably double bobbin, iron core step-up transformers having a 1:12 turns ratio and rated to pass 150 mA at 1,000 ohms over a frequency range of about 500 Hz to 12 KHz. Transformers 70, 78 are utilized for patient isolation between channel A and B outputs 32, 34 and the electronic circuitry of power muscle stimulator 10, as is well understood.

In use, a profile signal is selected by setting switch 124 to address the appropriate page of memory 122. The repetition rate of the waveform signal is similarly selected by appropriate setting of switch 106. The desired stim segment is selected by appropriate setting of switch 90.

The user or a technician will place electrodes 38, 48 on skin 40 of arm 42 in well-known fashion so that the electrodes are in overlying relationship with biceps muscles 44 and triceps muscles 50, respectively. Electrodes 38, 48 are coupled via wires 36, 46 to channel A and B outputs 32, 34, respectively.

A mechanical timer 200 is set to a desired exercise therapy time such as thirty minutes. When timer 200 is set, relay coil 202 is energized closing switch 150 to thereby couple generator signal 28 to output section 16 for application of stimulus signals to muscles 44, 50. Also, a high signal ($+V_1$) is applied to the clear input 204 of counter 120 allowing it to begin counting. Until then, counter 120 is held to a count of zero to avoid an instant surge of stimulus current applied to the arm 42 of the patient. As seen in FIG. 6, where the slow twitch profile signal is selected, no stimulus will be applied for the first 15 seconds until the ramp-up appears at 15 through 18 seconds into the profile signal. During this time, the waveform signal will be repeatedly applied as a stimulus signal, but at ever increasing amplitudes until a maximum is reached, at which time the maximum is maintained for 12 seconds followed by a 3 second ramp down to zero.

By appropriately setting respective input potentiometers 160, a desired amount of contraction of the muscles may be selected depending on the current health of the muscles and the extent of exercise desired. Further, potentiometers 160 may be independently adjusted to vary the amplitude of the stimulus signal 32 or stimulus signal 34 whereby to ensure that the levels of contraction of muscles 44, 50 generally offset one another. Thereafter, during the ramp up/down and maximum output periods, unloaded isometric exercise of muscle pairs 44, 50 is being achieved, substantially without creation of torque at elbow 54.

The muscle contracting portion of the stimulus signals are derived from the stim segments of the waveform signal. Preferably, the stim segment is comprised of a continuously varying, biphasic signal with no abrupt change in amplitude. A signal having such characteristics when applied to electrically stimulate muscles is less painful than signals not having such characteristics. Thus, as shown in FIG. 3, memory 88 includes on one of its pages a digital representation of a sinewave stim segment. A sinewave stim segment is a continuously varying, biphasic signal having opposite-polarity, equal amplitude portions $S_1$ and $S_2$ relative an average (here, zero) with one zero crossing 113 therebetween over one fundamental period of the stim segment. The fundamental period of stim segment 110 is preferably between about 300 and about 1,000 microseconds. The period may be selected by appropriate programming of memory 88 such as, by way of example, programming 192 consecutive words or locations of 256 available locations of memory 88 with data to produce a non-zero (except at the zero-crossing) continuously varying waveform during the stim segment, the remaining words or locations being programmed to provide zero amplitude output to thus provide rest portion(s) in addition to rest segment 112. In one embodiment, the period of stim segment 110 is about 750 microseconds by programming the selected page of memory 88 as shown in Table III.

The sinewave stim segment is provided to allow use of the power muscle stimulator 10 of the present invention with individuals that would otherwise find more conventional stimulation signals objectionably uncomfortable or painful. To further avoid abrupt changes in the signal, it is desired that the stim segment always start at zero. It is further desired that the profile signal be correlated to the stim segment to avoid abrupt changes in amplitude of the resulting stimulus signal to the muscles. To this end, synchronization is provided to ensure that waveform signal 24 will start at zero and produce the sinewave stim segment shown in FIG. 3 followed by the appropriate rest segment by tying the set and reset signals of flip-flop 102 to the same counter and clock. Similarly, clocking profile generator 18 from counter 86 ensures synchronization of waveform signal 24 to the profile signal 20 so that there is no sudden or abrupt change in the stimulus signal ultimately coupled to the muscles.

As will be appreciated, the stim segment shown in FIG. 3 is but one of the possible stim segments signals possible with stimulator 10 of the present invention. A preferred stim segment is provided in a different page of memory 88, as shown in Table IV. The preferred stim segment is believed to have characteristics allowing power contracting of muscles with reduced objectionable discomfort or pain, even to individuals suffering from no relevant nerve damage. A preferred stim segment is shown in FIG. 7.

Figure 7:
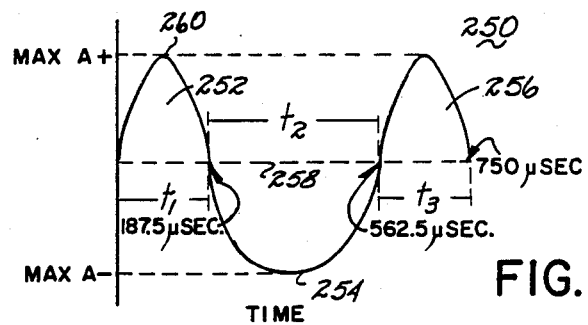
FIG. 7 is a preferred stim segment of a waveform signal generated by the waveform generator of FIG. 1 in accordance with principles of the present invention.

As seen in FIG. 7, preferred stim segment 250 has three portions 252, 254 and 256, each of which continuously varies from a reference 258 (here, zero) to a maximum amplitude (Max A+ and Max A−) and then back to zero. However, first and third portions 252, 256 have one polarity relative reference 258, and intermediate, second portion 254 an opposite polarity relative to reference 258. Thus, stim segment 250 is biphasic but would appear, if viewed on an oscilloscope, to have two humps like a camel's back during one repetition (i.e., during a fundamental period) of the stim segment. Thus, the preferred stim segment has a fundamental period during which it is continuous, biphasic, and camel-back. Although portions 252 and 256 are shown having positive polarity and portion 254 negative, the inverse would be acceptable, i.e., portions 252, 256 of negative polarity and portion 254 of positive polarity.

Significantly, the absolute magnitude of each of the three portions relative reference 258 is the same. Further significantly, the duration $t_1$ of portion 252 is equal to the duration $t_3$ of portion 256, and the duration $t_2$ of intermediate portion 254 is equal to the sum of $t_1$ and $t_3$ (or twice either $t_1$ or $t_3$). Although other durations could be selected, by way of example, memory 88 may be programmed as shown in Table IV such that $t_1+t_2+t_3=750$ microseconds, $t_1=t_3=187.5$ microseconds, and $t_2=375$ microseconds.

Due to time and amplitude relationships, the energy delivered to a muscle due to portion 254 is equal to twice the energy delivered to a muscle due to either of portions 252 and 256. That is, the magnitude of the integral of both the first and third portions 252 and 256 relative reference 258 is equal to the magnitude of the integral of the second portion 54 relative reference 258. Similarly, the fundamental frequency of each of the first and third portions 52, 256 is twice the fundamental frequency of second portion 254 (preferably about 5.33 KHz and 2.66 KHz, respectively).

It is believed that the foregoing, preferred, continuous, camel-back, biphasic stim segment 250 of the present invention allows for power contracting electrical muscle stimulation with substantially reduced risk of pain relative the sinewave stim segment, even for individuals suffering no relevant nerve damage. Further, the stim segments shown in FIGS. 3 and 7 in cooperation with the profile signals of FIGS. 4 and 5 are believed to also maximize training or the effective building of muscle mass.

Stimulator 10 may be powered from a 120 VAC supply through plug 300. Plug 300 is selectively coupled to power supplies PS1 and PS2 via on/off switch 302. Power supplies PS1 and PS2 include appropriate transformers, diode bridges and voltage regulators as are conventional to provide $+V_1$ from PS1 and each of $+V_2$ and $-V_2$ from PS2. Power supply PS1 produces $+V_1=5$ volts, for example, to provide a source of power for the digital logic circuitry as is conventional. Power supply PS2 produces $+V_2=12$ volts and $-V_2=-12$ volts, for example, to provide a source of power for amplifiers 68, 76, 96, 99 and 134. As indicated at 304, 306, the $+V_2$ and $-V_2$ outputs of PS2 are preferably capacitively coupled to ground through 6,800 microfarad capacitors to allow non-sagging of the stimulus signals 32, 34 during the stimulus time (when the profile signal is non-zero).

By virtue of the foregoing, there is thus provided an apparatus and method to accomplish isometric exercise of muscle associated with a rotatable limb substantially without creating torque at the rotational joint of the limb and without the need to externally load or restrain the limb. Further, where the preferred stim segment is employed in the waveform signal, muscle stimulation may be achieved with reduced risk of objectionable discomfort or pain, even at the high stimulus levels possible with the present invention.

Figure 8:
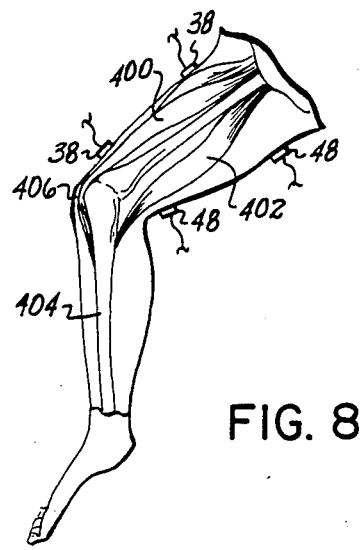
FIG. 8 is a diagram showing placement of electrodes to isometrically exercise quadriceps and hamstrings associated with a leg in further accordance with the principles of the present invention.

While the present invention has been illustrated by description of a preferred embodiment and while the preferred embodiment has been described in considerable detail, it is not the intention of the applicants to restrict or in any way limit the scope of the appended claims to such detail. Additional advantages and modifications will readily appear to those skilled in the art. For example, while the invention has been described in connection with the biceps and triceps muscles of the forearm as the antagonist muscle pair, other such muscle pairs are available in the body and it is believed they would benefit from the present invention as well. By way of example, the quadricep muscles 400 and hamstring muscles 402 associated with lower leg 404 may be isometrically stimulated without substantially creating torque at knee 406 about which lower leg 404 tends to rotate when quadricep muscles 400 or hamstring muscles 402 are stimulated. To this end, and as shown in FIG. 8, electrodes 38 may be applied to skin 408 overlaying quadricep muscles 400 and electrodes 48 applied to skin 408 overlaying hamstring muscles 402. Other muscle pairs include the flexor and extensor muscles associated with the wrist, and the gastrocnemius muscles and tibialis anterior muscles associated with the ankle, to name but a few. Additionally, although electrodes 38, 48 are shown as surface electrodes, electrodes could be coupled directly into the muscles. In that event, lower level power output from channels A and B should be employed. Finally, although only two stim segments and two profile signals are shown, memories 88, 112 may have more than two pages (and appropriate selector switches provided) wherein more stim segments and profile signals may be provided with stimulator 10. The invention in its broader aspects is therefore not limited to the specific details, representative apparatus and method, and illustrative example shown and described. Accordingly, departures may be made from such details without, departing from the spirit or scope of applicants general inventive concept.

TABLE I

| | SLOW TWITCH EXERCISE PROFILE (Hexadecimal) | | | | | | | | | | | | | | | |
|---|---|---|---|---|---|---|---|---|---|---|---|---|---|---|---|---|
| | $A_0-A_3$ | | | | | | | | | | | | | | | |
| $A_4-A_7$ | 0 | 1 | 2 | 3 | 4 | 5 | 6 | 7 | 8 | 9 | A | B | C | D | E | F |
| 0 | 00 | 00 | 00 | 00 | 00 | 00 | 00 | 00 | 00 | 00 | 00 | 00 | 00 | 00 | 00 | 00 |
| 1 | 00 | 00 | 00 | 00 | 00 | 00 | 00 | 00 | 00 | 00 | 00 | 00 | 00 | 00 | 00 | 00 |
| 2 | 00 | 00 | 00 | 00 | 00 | 00 | 00 | 00 | 00 | 00 | 00 | 00 | 00 | 00 | 00 | 00 |

TABLE I-continued
SLOW TWITCH EXERCISE PROFILE
(Hexadecimal)

| | | | | | | | | $A_0-A_3$ | | | | | | | | |
|---|---|---|---|---|---|---|---|---|---|---|---|---|---|---|---|---|
| $A_4-A_7$ | 0 | 1 | 2 | 3 | 4 | 5 | 6 | 7 | 8 | 9 | A | B | C | D | E | F |
| 3 | 00 | 00 | 00 | 00 | 00 | 00 | 00 | 00 | 00 | 00 | 00 | 00 | 00 | 00 | 00 | 00 |
| 4 | 00 | 00 | 00 | 00 | 00 | 00 | 00 | 00 | 00 | 00 | 00 | 00 | 00 | 00 | 00 | 00 |
| 5 | 00 | 00 | 00 | 00 | 00 | 00 | 00 | 00 | 00 | 00 | 00 | 00 | 00 | 00 | 00 | 00 |
| 6 | 00 | 00 | 00 | 00 | 00 | 00 | 00 | 00 | 00 | 00 | 00 | 00 | 00 | 00 | 00 | 00 |
| 7 | 00 | 00 | 00 | 0B | 17 | 22 | 2E | 39 | 45 | 51 | 5C | 68 | 73 | 7F | 86 | 96 |
| 8 | A2 | AD | B9 | C5 | D0 | DC | E7 | F3 | FF | FF | FF | FF | FF | FF | FF | FF |
| 9 | FF | FF | FF | FF | FF | FF | FF | FF | FF | FF | FF | FF | FF | FF | FF | FF |
| A | FF | FF | FF | FF | FF | FF | FF | FF | FF | FF | FF | FF | FF | FF | FF | FF |
| B | FF | FF | FF | FF | FF | FF | FF | FF | FF | FF | FF | FF | FF | FF | FF | FF |
| C | FF | FF | FF | FF | FF | FF | FF | FF | FF | FF | FF | FF | FF | FF | FF | FF |
| D | FF | FF | FF | FF | FF | FF | FF | FF | FF | FF | FF | FF | FF | FF | FF | FF |
| E | FF | FF | FF | FF | FF | FF | FF | FF | FF | F3 | E7 | DC | D0 | C5 | B9 | AD |
| F | A2 | 96 | 86 | 7F | 73 | 68 | 5C | 51 | 45 | 39 | 2E | 22 | 17 | 0B | 00 | 00 |

TABLE II
FAST TWITCH EXERCISE PROFILE
(Hexadecimal)

| | | | | | | | | $A_0-A_3$ | | | | | | | | |
|---|---|---|---|---|---|---|---|---|---|---|---|---|---|---|---|---|
| $A_4-A_7$ | 0 | 1 | 2 | 3 | 4 | 5 | 6 | 7 | 8 | 9 | A | B | C | D | E | F |
| 0 | 00 | 00 | 00 | 00 | 00 | 00 | 00 | 00 | 00 | 00 | 00 | 00 | 00 | 00 | 00 | 00 |
| 1 | 00 | 00 | 00 | 00 | 00 | 00 | 00 | 00 | 00 | 00 | 00 | 00 | 00 | 00 | 00 | 00 |
| 2 | 00 | 00 | 00 | 00 | 00 | 00 | 00 | 00 | 00 | 00 | 00 | 00 | 00 | 00 | 00 | 00 |
| 3 | 00 | 00 | 00 | 00 | 00 | 00 | 00 | 00 | 00 | 00 | 00 | 00 | 00 | 00 | 00 | 00 |
| 4 | 00 | 00 | 00 | 00 | 00 | 00 | 00 | 00 | 00 | 00 | 00 | 00 | 00 | 0B | 17 | 22 |
| 5 | 2E | 39 | 45 | 51 | 5C | 68 | 73 | 7F | 86 | 96 | A2 | AD | B9 | C5 | D0 | DC |
| 6 | E7 | F3 | FF | FF | F3 | E7 | DC | D0 | C5 | B9 | AD | A2 | 96 | 86 | 7F | 73 |
| 7 | 68 | 5C | 51 | 45 | 39 | 2E | 22 | 17 | 0B | 00 | 00 | 00 | 00 | 00 | 00 | 00 |
| 8 | 00 | 00 | 00 | 00 | 00 | 00 | 00 | 00 | 00 | 00 | 00 | 00 | 00 | 00 | 00 | 00 |
| 9 | 00 | 00 | 00 | 00 | 00 | 00 | 00 | 00 | 00 | 00 | 00 | 00 | 00 | 00 | 00 | 00 |
| A | 00 | 00 | 00 | 00 | 00 | 00 | 00 | 00 | 00 | 00 | 00 | 00 | 00 | 00 | 00 | 00 |
| B | 00 | 00 | 00 | 00 | 00 | 00 | 00 | 00 | 00 | 00 | 00 | 00 | 00 | 00 | 00 | 00 |
| C | 00 | 00 | 00 | 00 | 00 | 00 | 00 | 00 | 00 | 00 | 00 | 00 | 00 | 00 | 00 | 00 |
| D | 00 | 00 | 0B | 17 | 22 | 2E | 39 | 45 | 51 | 5C | 68 | 73 | 7F | 86 | 96 | A2 |
| E | AD | B9 | C5 | D0 | DC | E7 | F3 | FF | FF | F3 | DC | D0 | C5 | B9 | AD |
| F | A2 | 96 | 86 | 7F | 73 | 68 | 5C | 51 | 45 | 39 | 2E | 22 | 17 | 0B | 00 | 00 |

TABLE III
750 MICROSECOND SINEWAVE STIM SEGMENT
(Hexadecimal)

| | | | | | | | | $A_0-A_3$ | | | | | | | | |
|---|---|---|---|---|---|---|---|---|---|---|---|---|---|---|---|---|
| $A_4-A_7$ | 0 | 1 | 2 | 3 | 4 | 5 | 6 | 7 | 8 | 9 | A | B | C | D | E | F |
| 0 | 80 | 80 | 80 | 80 | 80 | 80 | 80 | 80 | 80 | 80 | 80 | 80 | 80 | 80 | 80 | 80 |
| 1 | 80 | 80 | 80 | 80 | 80 | 80 | 80 | 80 | 80 | 80 | 80 | 80 | 80 | 80 | 80 | 80 |
| 2 | 80 | 84 | 88 | 8C | 90 | 94 | 99 | 9D | A1 | A5 | A9 | AD | B1 | B5 | B8 | BC |
| 3 | C0 | C3 | C7 | CA | CE | D1 | D4 | D7 | DA | DD | E0 | E3 | E5 | E8 | EA | ED |
| 4 | EF | F1 | F3 | F4 | F6 | F8 | F9 | FA | FB | FC | FD | FE | FF | FF | FF | FF |
| 5 | FF | FF | FF | FF | FE | FE | FD | FC | FB | FA | F8 | F7 | F5 | F4 | F2 | F0 |
| 6 | EE | EB | E9 | E7 | E4 | E1 | DF | DC | D9 | D6 | D3 | CF | CC | C9 | C5 | C2 |
| 7 | BE | BA | B6 | B3 | AF | AB | A7 | A3 | 9F | 9B | 97 | 92 | 8E | 8A | 86 | 82 |
| 8 | 7D | 79 | 75 | 71 | 6D | 68 | 64 | 60 | 5C | 58 | 54 | 50 | 4C | 49 | 45 | 41 |
| 9 | 3D | 3A | 36 | 33 | 30 | 2C | 29 | 26 | 23 | 20 | 1E | 1B | 18 | 16 | 14 | 11 |
| A | 0F | 0D | 0B | 0A | 08 | 07 | 05 | 04 | 03 | 02 | 01 | 01 | 00 | 00 | 00 | 00 |
| B | 00 | 00 | 00 | 00 | 01 | 02 | 03 | 04 | 05 | 06 | 07 | 09 | 0B | 0C | 0E | 10 |
| C | 12 | 15 | 17 | 1A | 1C | 1F | 22 | 25 | 28 | 2B | 2E | 31 | 35 | 38 | 3C | 3F |
| D | 43 | 47 | 4A | 4E | 52 | 56 | 5A | 5E | 62 | 66 | 6B | 6F | 73 | 77 | 7B | 7F |
| E | 80 | 80 | 80 | 80 | 80 | 80 | 80 | 80 | 80 | 80 | 80 | 80 | 80 | 80 | 80 | 80 |
| F | 80 | 80 | 80 | 80 | 80 | 80 | 80 | 80 | 80 | 80 | 80 | 80 | 80 | 80 | 80 | 80 |

TABLE IV
750 MICROSECOND CAMEL-BACK STIM SEGMENT
(Hexadecimal)

| | | | | | | | | $A_0-A_3$ | | | | | | | | |
|---|---|---|---|---|---|---|---|---|---|---|---|---|---|---|---|---|
| $A_4-A_7$ | 0 | 1 | 2 | 3 | 4 | 5 | 6 | 7 | 8 | 9 | A | B | C | D | E | F |
| 0 | 80 | 80 | 80 | 80 | 80 | 80 | 80 | 80 | 80 | 80 | 80 | 80 | 80 | 80 | 80 | 80 |
| 1 | 80 | 80 | 80 | 80 | 80 | 80 | 80 | 80 | 80 | 80 | 80 | 80 | 80 | 80 | 80 | 80 |
| 2 | 80 | 88 | 90 | 99 | A1 | A9 | B1 | B8 | C0 | C7 | CE | D4 | DA | E0 | E5 | EA |
| 3 | EF | F3 | F6 | F9 | FB | FD | FF | FF | FF | FF | FE | FD | FB | F8 | F5 | F2 |
| 4 | EE | E9 | E4 | DF | D9 | D3 | CC | C5 | BE | B6 | AF | A7 | 9F | 97 | 8E | 86 |

TABLE IV-continued

750 MICROSECOND CAMEL-BACK STIM SEGMENT
(Hexadecimal)

| $A_4$-$A_7$ | \| | \| | \| | \| | \| | \| | \| | $A_0$-$A_3$ | \| | \| | \| | \| | \| | \| | \| |
|---|---|---|---|---|---|---|---|---|---|---|---|---|---|---|---|---|
| | 0 | 1 | 2 | 3 | 4 | 5 | 6 | 7 | 8 | 9 | A | B | C | D | E | F |
| 5 | 7D | 79 | 75 | 71 | 6D | 68 | 64 | 60 | 5C | 58 | 54 | 50 | 4C | 49 | 45 | 41 |
| 6 | 3D | 3A | 36 | 33 | 30 | 2C | 29 | 26 | 23 | 20 | 1E | 1B | 18 | 16 | 14 | 11 |
| 7 | 0F | 0D | 0B | 0A | 08 | 07 | 05 | 04 | 03 | 02 | 01 | 01 | 00 | 00 | 00 | 00 |
| 8 | 00 | 00 | 00 | 00 | 01 | 02 | 03 | 04 | 05 | 06 | 07 | 09 | 0B | 0C | 0E | 10 |
| 9 | 12 | 15 | 17 | 1A | 1C | 1F | 22 | 25 | 28 | 2B | 2E | 31 | 35 | 38 | 3C | 3F |
| A | 43 | 47 | 4A | 4E | 52 | 56 | 5A | 5E | 62 | 66 | 6B | 6F | 73 | 77 | 7B | 7F |
| B | 82 | 88 | 90 | 99 | A1 | A9 | B1 | B8 | C0 | C7 | CE | D4 | DA | E0 | E5 | EA |
| C | EF | F3 | F6 | F9 | FB | FD | FF | FF | FF | FF | FE | FD | FB | F8 | F5 | F2 |
| D | EE | E9 | E4 | DF | D9 | D3 | CC | C5 | BE | B6 | AF | A7 | 9F | 97 | 8E | 86 |
| E | 80 | 80 | 80 | 80 | 80 | 80 | 80 | 80 | 80 | 80 | 80 | 80 | 80 | 80 | 80 | 80 |
| F | 80 | 80 | 80 | 80 | 80 | 80 | 80 | 80 | 80 | 80 | 80 | 80 | 80 | 80 | 80 | 80 |

What is claimed is:

1. A method of isometrically stimulating muscles associated with a limb adapted to rotate at a joint, comprising:

substantially simultaneously:
(1) applying a first electrical stimulus to an agonist muscle associated with the limb to contract the agonist muscle whereby to tend to rotate the limb in one direction; and
(2) applying a second electrical stimulus to an antagonist muscle associated with the limb to contract the antagonist muscle whereby to tend to rotate the limb in another, opposite direction;
wherein the first and second electrical stimuli being effective to cause contraction of the respective muscles in an amount such that tendency of the limb to rotate in one direction is offset by a substantially equal tendency to rotate in the opposite direction whereby to isometrically stimulate the muscles substantially without creation of a net torque at the joint.

2. The method of claim 1, each of the first and second electrical stimuli having a characteristic waveshape, the characteristic waveshapes of the first and second stimuli being substantially identical.

3. The method of claim 1, the electrical stimuli each including a continuous biphasic segment which, during a fundamental period thereof, is camel-back having two portions having respective maximum amplitudes of a first polarity relative a reference separated by an intermediate portion having a maximum amplitude of a second polarity relative the reference.

4. The method of claim 1 further comprising:
generating an electrical signal having selected characteristics;
amplifying in a first channel the electrical signal to generate the first electrical stimulus for application to the agonist muscle; and
amplifying in a second channel the electrical signal to generate the second electrical stimulus for application to the antagonist muscle.

5. The method of claim 4 further comprising:
selecting at least some of the characteristics of the electrical signal.

6. The method of claim 4, generating the electrical signal including:
generating a selected, periodically repeating waveform signal;
generating a selected, periodically repeating profile signal; and
combining the waveform signal and the profile signal.

7. The method of claim 4, generating the electrical signal including generating a waveform signal including a stim segment and a variable length rest segment, the method further comprising selecting the length of the rest segment.

8. The method of claim 4, generating the electrical signal including generating a waveform signal including one of a plurality of selectable stim segments, the method further comprising selecting one of said stim segments.

9. The method of claim 8, at least some of the stim segments being continuous and biphasic.

10. The method of claim 9, at least one of the stim segments being continuous and biphasic, and, during a fundamental period thereof, camel-back having two portions having respective maximum amplitudes of a first polarity relative a reference separated by an intermediate portion having a maximum amplitude of a second polarity relative the reference.

11. The method of claim 10, the two portions having substantially identical durations and maximum amplitudes, the intermediate portion having a maximum amplitude equal, but of opposite polarity, to the maximum amplitude of either of the two portions, and a duration twice the duration of either of the two portions.

12. A method of reduced pain functional electrical muscle stimulation, comprising:
generating for application to a muscle a stim signal which is continuous and biphasic, and during a fundamental period thereof, camel-back having two portions having respective maximum amplitudes of a first polarity relative a reference separated by an intermediate portion having a maximum amplitude of a second polarity relative the reference, whereby to power contract the muscle without objectionable discomfort or pain.

13. The method of claim 12, the two portions having substantially identical durations and maximum amplitudes, the intermediate portion having a maximum amplitude equal, but of opposite polarity, to the maximum amplitude of either of the two portions, and a duration twice the duration of either of the two portions.

14. The method of claim 12, the stim signal having characteristics as follows:

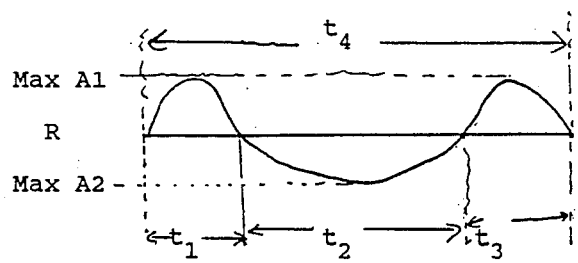

wherein R is a reference, $t_4$ is the fundamental period of the stim signal, $t_1$ is the duration of a first portion of the stim signal having a first polarity relative R and a maximum amplitude of Max A1, $t_2$ is the period of a second portion of the stim signal having a second polarity relative R and a maximum amplitude of Max A2, $t_3$ is the period of a third portion of the stim signal having the first polarity and a maximum amplitude of Max A1, and wherein $t_1 + t_2 + t_3 = t_4$ and $t_1 + t_3 = t_2$.

15. The method of claim 14 wherein $t_1 = t_3$.

16. The method of claim 14 wherein the energy contained in the first portion plus the energy contained in the third portion is equal in magnitude to the energy contained in the second portion.

17. Apparatus for isometrically stimulating muscles associated with a limb adapted to rotate at a joint, comprising:
   stimulator means for generating first and second electrical stimulus signals having respective characteristics;
   channel means coupled to the stimulator means for substantially simultaneously applying the first and second electrical stimulus signals to respective agonist and antagonist muscles associated with the limb, the first electrical stimulus signal being effective to contract the agonist muscle whereby to tend to rotate the limb in one direction, the second electrical stimulus signal being effective to contract the antagonist muscle whereby to tend to rotate the limb in another, opposite direction, the first and second electrical stimulus signals being effective to cause contraction of the respective muscles in an amount such that tendency of the limb to rotate in one direction is offset by a substantially equal tendency to rotate in the opposite direction whereby to isometrically stimulate the muscles substantially without creation of a net torque at the joint.

18. The apparatus of claim 17, each of the first and second electrical stimulus signals having a characteristic waveshape, the characteristic waveshapes of the first and second electrical stimulus signals being substantially identical.

19. The apparatus of claim 17, the stimulator means including:
   generator means for generating an electrical signal having selected characteristics;
   first amplifier means coupled to the generator means for generating the first electrical stimulus signal and coupling same to the channel means for application to the agonist muscle; and
   second amplifier means coupled to the generator means for generating the second electrical stimulus signals and coupling same to the channel means for application to the antagonist muscle.

20. The apparatus of claim 19, the channel means including:
   first isolation means coupled to the first amplifier means for applying the first electrical stimulus signal to the agonist muscle; and
   second isolation means coupled to the second amplifier means for applying the second electric stimulus signal to the antagonist muscle.

21. The apparatus of claim 19, the stimulator means further including:
   means for selecting at least some of the characteristics of the electrical signal.

22. The apparatus of claim 19, the generator means including:
   waveform generator means for generating a selected, periodically repeating waveform signal;
   profile generator means for generating a selected, periodically repeating profile signal; and
   means for combining the waveform signal and the profile signal whereby to generate the electrical signal.

23. The apparatus of claim 19, the generator means including:
   means for generating a stim segment;
   means for generating a variable length rest segment; and
   means for selecting the length of the rest segment.

24. The apparatus of claim 19, the generator means including:
   means for generating a plurality of stim segments; and
   means for selecting one of the stim segments to be generated.

25. The apparatus of claim 19, the generator means including:
   means for generating a stim segment, the stim segment being continuous and biphasic, and, during a fundamental period thereof, camel-back having two portions having respective maximum amplitudes of a first polarity relative a reference, separated by an intermediate portion having a maximum amplitude of a second polarity relative the reference.

26. The apparatus of claim 25, the two portions having substantially identical durations and maximum amplitudes, the intermediate portion having a maximum amplitude equal, but of opposite polarity, to the maximum amplitude of either of the two portions, and a duration twice the duration of either of the two portions.

27. An apparatus for functional electrical stimulation of muscle with reduced pain comprising:
   means for generating a stim signal for application to a muscle; and
   means for applying the stim signal to the muscle, the stim signal being continuous and biphasic, and, during a fundamental period thereof, camel-back having two portions having respective maximum amplitudes of a first polarity relative a reference, separated by an intermediate portion having a maximum amplitude of a second polarity relative the reference whereby to power contract the muscle without objectionable discomfort or pain.

28. The apparatus of claim 27, the two portions having substantially identical durations and maximum amplitudes, the intermediate portion having a maximum amplitude equal, but of opposite polarity, to the maximum amplitude of either of the two portions, and a duration twice the duration of either of the two portions.

29. The apparatus of claim 27, the stim signal having characteristics as follows:

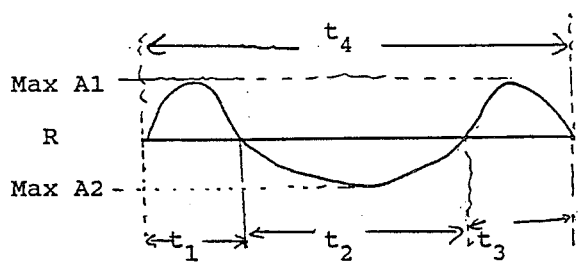

wherein R is a reference, $t_4$ is the fundamental period of the stim signal, $t_1$ is the duration of a first portion of the stim signal having a first polarity relative R and a maximum amplitude of Max A1, $t_2$ is the period of a second portion of the stim signal having a second polarity relative R and a maximum amplitude of Max A2, $t_3$ is the period of a third portion of the stim signal having the first polarity and a maximum amplitude of Max A1, and wherein $t_1+t_2+t_3=t_4$ and $t_1+t_3=t_2$.

30. The apparatus of claim 29 wherein $t_1=t_3$.

31. The apparatus of claim 29 wherein the energy contained in the first portion plus the energy contained in the third portion is equal in magnitude to the energy contained in the second portion.

32. The apparatus of claim 27, the means for generating including:
first means for digitally generating a plurality of multi-bit outputs representing the stim signal;
second means coupled to the first means for producing an analog signal corresponding to the multi-bit outputs, the analog signal being proportional to the stim signal; and
amplifier means coupling the analog signal from the converter means to the means for applying whereby to amplify the analog signal to provide the stim signal.

33. A method of isometrically stimulating the biceps and triceps muscles of an arm, comprising: substantially simultaneously:
(1) applying a first electrical stimulus to the biceps muscle to contract same whereby to tend to rotate the forearm in one direction relative the elbow; and
(2) applying a second electrical stimulus to the triceps muscle to contract same whereby to tend to rotate the forearm in another, opposite direction relative the elbow;
wherein the first and second electrical stimuli being effective to cause contraction of the respective muscles in an amount such that tendency of the forearm to rotate in one direction is offset by a substantially equal tendency to rotate in the opposite direction whereby to isometrically stimulate the muscles substantially without creation of a net torque at the elbow.

34. A method of isometrically stimulating the quadriceps and hamstring muscles of a leg, comprising: substantially simultaneously:
(1) applying a first electrical stimulus to the quadriceps muscle to contract same whereby to tend to rotate the lower leg in one direction relative the knee; and
(2) applying a second electrical stimulus to the hamstring muscle to contract same whereby to tend to rotate the lower leg in another, opposite direction relative the knee;
wherein the first and second electrical stimuli being effective to cause contraction of the respective muscles in an amount such that tendency of the lower leg to rotate in one direction is offset by a substantially equal tendency to rotate in the opposite direction whereby to isometrically stimulate the muscles substantially without creation of a net torque at the knee.

* * * * *